United States Patent
Barbato et al.

(10) Patent No.: US 7,273,452 B2
(45) Date of Patent: Sep. 25, 2007

(54) VISION CATHETER SYSTEM INCLUDING MOVABLE SCANNING PLATE

(75) Inventors: Louis J. Barbato, Franklin, MA (US); Mark A. Hamm, Lynnfield, MA (US); Yem Chin, Burlington, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 488 days.

(21) Appl. No.: 10/793,483

(22) Filed: Mar. 4, 2004

(65) Prior Publication Data

US 2005/0197534 A1 Sep. 8, 2005

(51) Int. Cl.
*A61B 1/06* (2006.01)
*A61B 1/04* (2006.01)

(52) U.S. Cl. ...................... 600/173; 600/109

(58) Field of Classification Search ............... 600/101, 600/103, 109, 129, 173; 348/199, 201
See application file for complete search history.

(56) References Cited

U.S. PATENT DOCUMENTS

| | | | |
|---|---|---|---|
| 3,266,059 A | | 8/1966 | Stelle |
| 3,572,325 A | | 3/1971 | Bazell et al. |
| 4,432,349 A | | 2/1984 | Oshiro |
| 4,816,909 A | | 3/1989 | Kimura et al. |
| 4,846,155 A | | 7/1989 | Kimura |
| 4,870,951 A | | 10/1989 | Suzuki |
| 5,060,632 A | | 10/1991 | Hibino et al. |
| 5,506,912 A | * | 4/1996 | Nagasaki et al. ............ 382/103 |
| 5,579,125 A | * | 11/1996 | Owen ............................ 386/1 |
| 5,976,074 A | | 11/1999 | Moriyama |
| 6,013,025 A | | 1/2000 | Bonne et al. |
| 6,294,775 B1 | | 9/2001 | Seibel et al. |
| 6,485,413 B1 | * | 11/2002 | Boppart et al. ............. 600/160 |
| 2001/0017654 A1 | * | 8/2001 | Muto ........................ 348/207 |
| 2001/0055462 A1 | | 12/2001 | Seibel |
| 2002/0139920 A1 | | 10/2002 | Seibel et al. |
| 2003/0045778 A1 | | 3/2003 | Ohline et al. |
| 2003/0130562 A1 | | 7/2003 | Barbato et al. |

FOREIGN PATENT DOCUMENTS

| | | |
|---|---|---|
| JP | 1-237613 | 9/1989 |
| WO | WO 2005/009513 A2 | 2/2005 |

* cited by examiner

*Primary Examiner*—John P. Leubecker
*Assistant Examiner*—Philip R Smith
(74) *Attorney, Agent, or Firm*—Christensen O'Connor Johnson Kindness PLLC

(57) ABSTRACT

A disposable imaging catheter that produces high resolution, color images comparable to those obtained from an endoscope. The device may also be made to function as a guidewire. The device may also include a sheath which slides over the catheter body for stiffening and which may include a working channel for accepting interventional devices, as well as LEDs to illuminate the field of view. The vision catheter system includes a detector assembly, scanning mechanism, and distal objective lens. In one embodiment, a photodetector is mated to a lens/pinhole assembly that allows the detector to read light from a small discrete point. This assembly is then scanned in raster or spiral patterns via electric wire coils that actuate a magnetic scan plate to read the area of interest. By adding a fixed objective lens, such as an aspheric lens that is attached to the distal tip of the catheter body, the field of view or acceptance angle of the system is magnified, yielding a wide angle image similar to that commonly obtained from an endoscope.

12 Claims, 3 Drawing Sheets

VISION CATHETER SYSTEM INCLUDING MOVABLE SCANNING PLATE

FIELD OF THE INVENTION

The present invention relates to medical devices, and in particular, to a catheter with imaging capabilities.

BACKGROUND OF THE INVENTION

Many medical interventional procedures are dependent on endoscopes to deliver diagnostic and therapeutic catheters to GI, URO, and biliary locations throughout the body. In these types of procedures, the area for maneuvering the endoscope is limited by the working channel diameter. Further limitations regarding the areas that are accessible to the endoscope are due to the physical constraints caused the size and stiffness of the endoscope. Furthermore, with regard to the comfort of the patient, endoscopic procedures are often very painful and require sedation.

A typical endoscope has an illumination channel and an imaging channel, both of which may be made of a bundle of optical fibers. The illumination channel is coupled to a light source to illuminate an internal body cavity of a patient, and the imaging channel transmits an image created by a lens at the distal end of the endoscope to a connected camera unit or display device. As an alternative to an imaging channel made of a bundle of optical fibers, a semiconductor-type camera can also be attached onto the distal tip. One drawback of this alternative is that such cameras are relatively large in size, in comparison to the dimensions needed for certain surgical procedures. Another issue with either the semiconductor-type camera or the bundle of fibers is that the ability to see a larger area requires moving the camera or the bundle of fibers. This type of movement is relatively complex to implement, and requires even more area. Furthermore, while endoscopes are a proven technology, they are relatively complex and expensive to manufacture.

Certain known systems have attempted to produce high-resolution images with a small diameter catheter, most involving optical fibers or fiber imaging bundles in some way. The cost and complexity of an imaging bundle-based vision catheter severely limits its application in the GI and URO fields. The size and number of individual light carrying fibers that comprise an imaging fiber bundle limit the image resolution. For these and other reasons, endoscopes have moved to imaging arrays at the distal tip of the endoscope, which are cheaper, and produce higher resolution images, while increasing the life span of the scope. Due to the size of the arrays and the processing that must take place near the arrays, the endoscope diameters are generally quite large. In addition, they usually require a light source and working channel to allow the clinician to perform therapeutic procedures.

The present invention is directed to an apparatus that overcomes the foregoing and other disadvantages. More specifically, the present invention is directed to a much smaller profile catheter-based device that provides imaging capabilities that are comparable to those of endoscopes.

SUMMARY OF THE INVENTION

The present invention is directed to a vision catheter system. In accordance with one aspect of the invention, the device is in the form of a disposable imaging catheter that produces high-resolution color images that are comparable to those obtained from an endoscope. The device may also function as a guidewire to guide larger devices to areas of interest to facilitate diagnosis and treatment within various lumens of the human body, such as the vasculature, GI, urology (URO) and biliary tracts. The vision catheter system of the present invention is intended to reduce or eliminate the dependence on endoscopes while providing comparable imaging capabilities for many areas within the human body including certain areas that are inaccessible to endoscopes. The device is generally applicable in environments (even those outside the medical field) where low cost, remote imaging is needed.

In accordance with one aspect of the invention, the vision catheter system of the present invention is operable to provide usable images of anatomy that may be beyond the reach of a typical endoscope. In one application, the vision catheter system may be passed through the working channel of an endoscope, and may extend far beyond the distal tip of the endoscope.

In accordance with another aspect of the invention, the vision catheter system may be utilized without an endoscope, where the device acts as an imaging guidewire. In such applications, interventional surgical devices may be passed over the device and guided to the site of interest.

In accordance with another aspect of the invention, the vision catheter system may provide usable images with a large field of view, such as may be useful for navigating in lumens, such as the vasculature, GI, URO, and biliary tracts. It can also provide images utilizing a small field of view, such as may be useful for guiding snares or forceps, monitoring tissue color, and being utilized with fluorescence capabilities for detecting margins of cancerous or displastic tissues.

In accordance with another aspect of the invention, the vision catheter system may include a stiffening sheath that slides over the catheter body. In another embodiment, a multi-lumen sheath may be provided that slides over the catheter body and which includes a working channel to accept interventional devices. In yet another embodiment, the stiffening sheath and multi-lumen sheath may be combined to form a multi-lumen extrusion with a working channel. The sheath may also house LEDs or laser diodes to illuminate the field of view. In one particular implementation, three LEDs or laser diodes may be provided so as to provide three colors or wavelengths. These LEDs or laser diodes may be located on the sheath itself, or may be located on a proximal scanning plate.

In accordance with another aspect of the invention, the vision catheter system includes a detector assembly, scanning mechanism, and distal objective lens. In one embodiment, a photodetector is mated to a lens/pinhole assembly that allows the detector to read light from a small discrete point. This assembly is then scanned in raster or spiral patterns via electric wire coils that actuate a magnetic scan plate to read the area of interest. By adding a fixed objective lens, such as an aspheric lens that is attached to the distal tip of the catheter body, the field of view or acceptance angle of the system is magnified, yielding a wide angle image similar to that commonly obtained from an endoscope.

It will be appreciated that the vision catheter system of the present invention includes components that are widely available and that can easily be assembled. The simple design thus allows for the production of catheters that are relatively inexpensive and disposable and which have imaging capabilities while still remaining relatively small in diameter.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
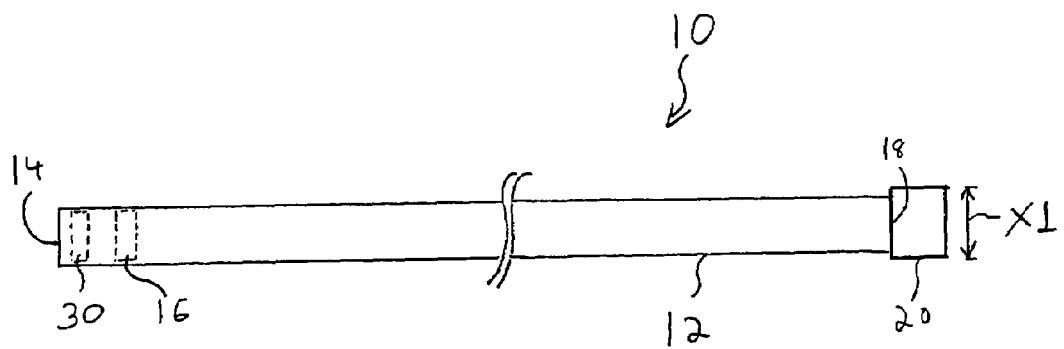
FIG. 1 shows a vision catheter system formed in accordance with the present invention.

FIG. 1 is a diagram of a vision catheter system 10 formed in accordance with the present invention. The vision catheter system 10 includes a flexible catheter body 12 having a distal end 14. The vision catheter system 10 also includes a scanning mechanism and detector assembly 16, which will be described in more detail below with reference to FIG. 4.

In one embodiment, the scanning mechanism and detector assembly 16 causes a scan to occur of an image at the distal end 14 of the catheter body 12. The scanning effect causes the field of view that is sensed by the distal end 14 to effectively increase. The sensed image may be transferred to a computer or processor, and may further be recorded and/or displayed on a monitor. The vision catheter system 10 also includes a distal objective lens 30 that is placed in front of the scanning mechanism and detector assembly 16. The distal objective lens 30 is equipped with a flush port to clean the lens. In one embodiment, the distal objective lens 30 (FIG. 1) may be an aspheric lens that is attached to the distal tip of the catheter body, through which the field of view or acceptance angle of the system is magnified, yielding a wide angle image such as that commonly obtained from an endoscope.

In one embodiment, the vision catheter system 10 can be equipped with two objective lenses, such as gradient index (GRIN) rod lenses that also yield stereo vision, which can be made to provide a three-dimensional image with perspective. This embodiment can include two detector/lens assemblies, which may be located on the same scanning mechanism. The two images can then be combined to create a three-dimensional image with perspective. Because of the small diameter, cylindrical objective lenses can be spaced slightly apart or near the outer diameter of the sheath. In addition, a central guidewire lumen can be provided to allow access to more remote areas within the body.

The catheter body 12 also includes a proximal end 18 that has an electrical connector 20. The electrical connector 20 has a dimension X1 which is designed to be small enough to allow backloading of larger sheaths, as will be described in more detail below with reference to FIGS. 2 and 3. The electrical connector 20 provides electrical connections for the catheter body 12, such that the image signals from the imaging fibers can be received and processed. In one embodiment, the vision catheter system 10 may serve as a guidewire with a single pixel scanning camera that operates on a principle similar to the way a television works, which can be used by itself or in conjunction with other components to increase its capabilities. In one embodiment, the vision catheter system 10 may be formed as a 2-3 mm profile catheter that provides high resolution images.

Figure 2:
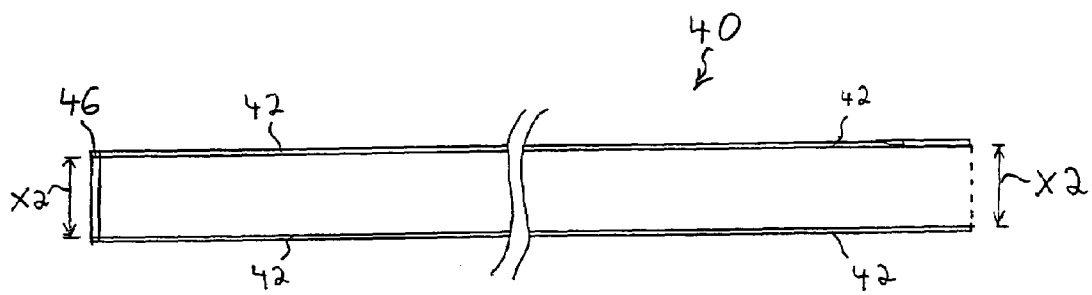
FIG. 2 shows a stiffening sheath that slides over the catheter body of FIG. 1.

FIG. 2 is a diagram of a stiffening sheath 40 that slides over the catheter body 12. The stiffening sheath 40 includes stiffening walls 42, and has a lens 46 located on the distal tip. The stiffening sheath 40 has an internal diameter X2, which is intended to be larger than the external diameter X1 of the electrical connector 20 of the vision catheter system 10, such that the stiffening sheath 40 can be backloaded over the catheter body 12.

In one embodiment, an objective lens is housed at the distal tip of the stiffening sheath 40. This allows the user to change the distance between the detector/lens assembly and the objective lens, thus providing a zoom capability. While this tends to increase the profile of the system, it also may be designed to allow room for a working channel, which provides for additional interventional capabilities in a device that is still relatively small in diameter.

Figure 3:
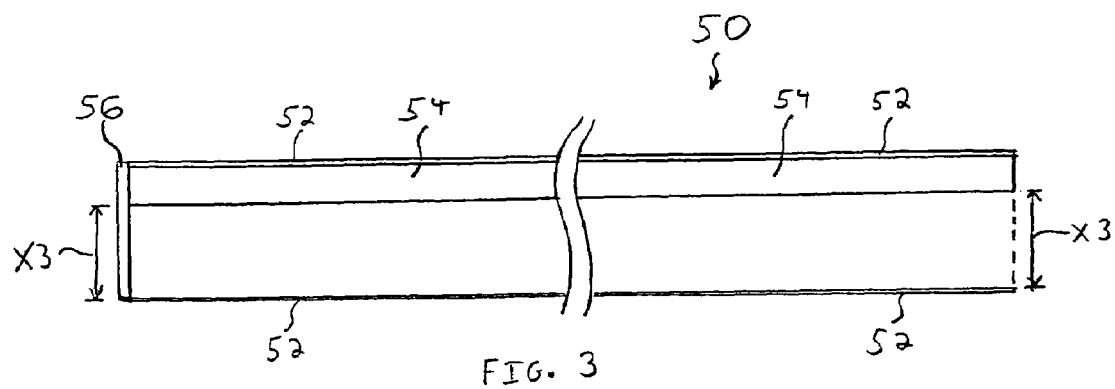
FIG. 3 shows a multi-lumen sheath that slides over the catheter body of FIG. 1 and which includes a working channel to accept interventional devices.
Figure 4:
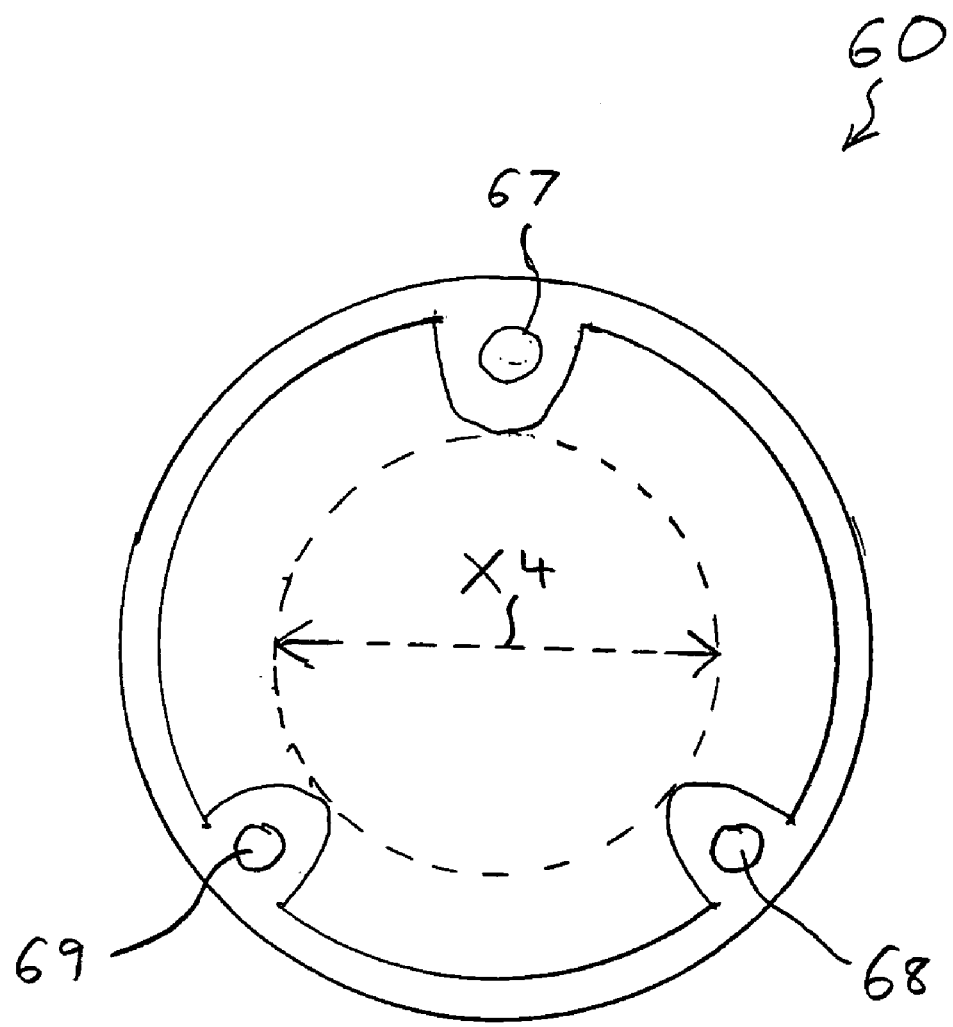
FIG. 4 is a cross-sectional view of a sheath that slides over the catheter body of FIG. 1 and which includes three laser diodes for illuminating a field of view.

FIG. 3 is a diagram of a multi-lumen sheath 50. The multi-lumen sheath 50 has walls 52 and includes a working channel 54 that can accept the usual interventional devices currently used in the medical field, and also has a lens 56 located on the distal tip. The multi-lumen sheath 50 has an internal diameter X3, which is intended to be larger than the external diameter X1 of the electrical connector 20, such that the multi-lumen sheath 50 can be backloaded over the catheter body 12. In one embodiment, the stiffening sheath 40 of FIG. 2 and multi-lumen sheath 50 of FIG. 3 may be combined and may be formed of a multi-lumen extrusion with a working channel. As illustrated in FIG. 4, in one embodiment, the sheath 60 may also house three LEDs or laser diodes 67, 68, and 69 to illuminate the field of view. The sheath 60 has an internal diameter X4, which is intended to be larger than the external diameter X1 of the electrical connector 20 of the vision catheter system 10, such that the sheath 60 can be backloaded over the catheter body 12. In one particular implementation, the LEDs or laser diodes may be made to provide three colors or wavelengths. These LEDs or laser diodes may be located on the sheath or they may be located on the proximal scanning plate, as will be described in more detail below with respect to FIG. 5.

Figure 5:
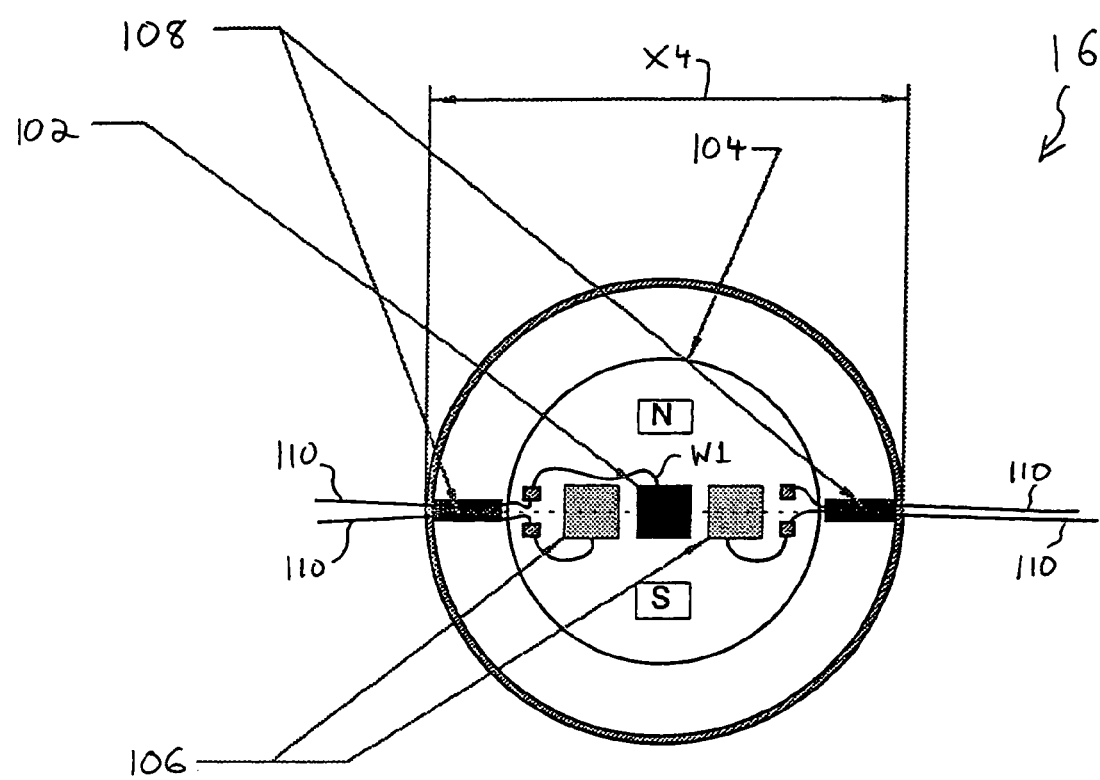
FIG. 5 is a cross-sectional view of a scanning mechanism and detector assembly within the vision catheter system of FIG. 1.

FIG. 5 is a cross-sectional view of one embodiment of the scanning mechanism and detector assembly 16 of the vision catheter system 10. As shown in FIG. 5, the scanning mechanism and detector assembly 16 includes a detector 102, a scanning plate 104, emitters 106, torsion springs 108, and electrical conductors 110. The detector 102 is coupled to the external electronics by a wire W1.

In one embodiment, the detector 102 is a photodetector that is mated to a lens/pinhole assembly that allows the detector 102 to read light from a small discrete point, while rejecting all light from the remainder of the field of view. This assembly is then scanned in raster or spiral patterns via electric wire coils that actuate the magnetic scan plate 104 to read the object or area of interest. In other embodiments, other scanning schemes may also be utilized. In one embodiment, the wire W1 which connects to the detector 102 may be designed to be a small solid conductor wire, which is flexed by the scanning plate 104 motion, and may be intended to break due to fatigue after several hours of operation. This feature can be intended to ensure that a version of the vision catheter system 10, which is made to be disposable for sanitary and other reasons, will not be reused. In one embodiment, the torsion type springs 108 are generally intended to have a resonant frequency at or near the desired frequency of operation. The electrical conductors 110 traverse the torsion springs 108, thus minimizing breakage during the scan.

After the scan, the imaging signal information is then assembled by a computer via the electrical connector 20 (see FIG. 1) to form an image. In one embodiment, false color mapping (which is used in both CCD or CMOS imaging arrays) may then be utilized to calculate color.

In one embodiment, the scanning plate 104 may be designed and built as a photo etched component and a printed circuit designed to accept the photo-detectors and LEDs to provide a smaller scanning plate and more robust assembly. The manufacturing process may utilize existing technology, such as EDM, laser machining, or chemical etching. Electrical circuits can also be deposited onto the scanning plate using known industrial processes. In one embodiment, the scanning plate 104 may be designed and built using MEMS technology. In one implementation utilizing MEMS technology, the device can be fabricated in a 1 mm package.

In another embodiment, as nanotechnology processing improves, the vision catheter system 10 can be fabricated in an even smaller package. In addition, by using selected illumination wavelengths (e.g., 1500 nanometers) imaging through blood may be made possible by utilizing certain polarization techniques. The small size of the camera due to nanotechnology, and the ability to image through blood, can enable the vision catheter system to be utilized in certain coronary or other applications.

It will be appreciated that the present invention provides a vision catheter system that is relatively easy to build and which can be made from widely available components. Due to the modular design, simple, low cost components and extrusions can be utilized. The vision catheter system can be formed as a disposable imaging catheter that produces high resolution, color images comparable to those obtained from an endoscope. The device may also function as a guidewire to locate and guide larger devices to the areas of interest to facilitate diagnosis and treatment. The system reduces or eliminates the dependence on endoscopes while providing comparable images of many areas within the human body including even certain areas that are inaccessible to endoscopes. The device is also applicable outside the medical field where low cost, remote imaging is desired.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A vision catheter, comprising:
    a shaft having a proximal end and a distal end and a lumen therein; and
    a scanning plate supported in the lumen of the shaft by two or more springs, the scanning plate including a detector that produces an imaging signal, wherein the scanning plate interacts with electric wire coils to move the scanning plate within the lumen of the shaft, and wherein the two or more springs comprise torsion springs positioned on opposite sides of the scanning plate.

2. The vision catheter of claim 1, wherein the scanning plate includes one or more magnets positioned orthogonally to the torsion springs.

3. The vision catheter of claim 2, wherein the one or more magnets include two magnets that have poles aligned in opposite directions.

4. The vision catheter of claim 1, wherein the scanning plate has a desired frequency of movement in the lumen of the shaft and the torsion springs have a resonant frequency at the desired frequency of movement.

5. The vision catheter of claim 1, wherein the scanning plate includes one or more light emitters.

6. The vision catheter of claim 1, wherein the vision catheter is a single-use catheter.

7. The vision catheter of claim 1, further comprising a distal objective lens.

8. The vision catheter of claim 7, wherein the distal objective lens is disposed at the distal end of the shaft.

9. The vision catheter of claim 7, wherein the distal objective lens is an aspheric lens.

10. The vision catheter of claim 1, further comprising at least two gradient index lenses.

11. A vision catheter, comprising:
    a shaft having a proximal end, a distal end, and an opening in the shaft; and
    a scanning plate that is suspended at opposite edges within the opening of the shaft, the scanning plate further including a detector that produces imaging signals and one or more magnets that interact with electric coils to pivot the scanning plate within the opening, wherein the detector is connected to a wire which flexes as the scanning plate pivots, and wherein the wire is positioned to break after a predetermined time of pivoting the scanning plate.

12. The vision catheter of claim 11, wherein the scanning plate is suspended in the opening with a pair of torsion springs positioned on opposite edges of the scanning plate.

\* \* \* \* \*